(12) United States Patent
Suzuki (10) Patent No.: US 7,572,009 B2
(45) Date of Patent: Aug. 11, 2009

(54) METHOD AND APPARATUS FOR PROCESSING AN EYE FUNDUS IMAGE

(75) Inventor: Takayoshi Suzuki, Hamamatsu (JP)

(73) Assignee: Kowa Company Ltd. (JP)

( * ) Notice: Subject to any disclaimer, the term of this patent is extended or adjusted under 35 U.S.C. 154(b) by 254 days.

(21) Appl. No.: 11/607,316

(22) Filed: Nov. 30, 2006

(65) Prior Publication Data

US 2007/0132951 A1    Jun. 14, 2007

(30) Foreign Application Priority Data

Dec. 8, 2005   (JP) ............................. 2005-354280

(51) Int. Cl.
  *A61B 3/14*    (2006.01)
  *A61B 3/08*    (2006.01)
(52) U.S. Cl. ...................... 351/206; 351/201
(58) Field of Classification Search ................. 351/201, 351/206
  See application file for complete search history.

(56) References Cited

U.S. PATENT DOCUMENTS 6,454,410 B1 *   9/2002   Berger et al. ................. 351/206
7,318,643 B2 *   1/2008   Kushida ....................... 351/205
2005/0083484 A1 *   4/2005   Sekiguchi .................... 351/206
2005/0270485 A1 *  12/2005   Matsumoto ................... 351/206

OTHER PUBLICATIONS

Anonymous, "PhotoScope Pro" [online] Jul. 19, 2004, XP002436163. Retrieved from the Internet: URL:http://www.pokescope.com/downloads.html>[retrieved on Jun. 4, 2007] Overview, Cropping, Stereo Formats, Viewing Functions, Zooming.
Crespo et al. (editors), "Lecture Notes in Computer Science:Medical Data Analysis", vol. 2199 [online] 2001, Springer, Berlin/Heidelberg, XP002436202. Retrieved from the Internet:URL:http://www.springerlink.com/content14698 ludfbm 9862b/>, pp. 282-287.

\* cited by examiner

*Primary Examiner*—Jordan M. Schwartz
(74) *Attorney, Agent, or Firm*—Adams & Wilks (57) ABSTRACT

A left parallax image and a right parallax image for a fundus of the same eye being examined are captured and recorded, and at least one of the two images is displayed. An image in a prescribed area is clipped from the displayed image, and an image in an area that corresponds to the area of the clipped image is clipped from the other image. The two clipped images are then enlarged and displayed on a stereo monitor in a left-right alignment. In such a configuration, when an area to be displayed at a high-magnification is specified for one of the images, clipping and high magnification processes may be performed also for the other image. This allows stereoscopic observations of an eye fundus at high magnification to readily be performed.

5 Claims, 7 Drawing Sheets

METHOD AND APPARATUS FOR PROCESSING AN EYE FUNDUS IMAGE

BACKGROUND OF THE INVENTION

1. Field of the Invention

The present invention relates to a method and apparatus for processing an eye fundus image, and in particular relates to a method and apparatus for processing an eye fundus image to display an eye fundus image in a manner that allows an eye fundus to be enlarged and stereoscopically observed.

2. Description of the Prior Art

A demand has traditionally existed for viewing an eye fundus in a stereoscopic shape for use in eye fundus examinations. Methods for stereoscopically viewing an optic cup of an eye fundus or the like have been proposed wherein an eye fundus camera having a two-aperture photographic stop provided with left-right parallax is used to capture an image of an eye fundus with each of the photographic stop and the captured images are then aligned side-by-side, displayed on a monitor and observed using a stereoscope.

In such instances, the relative positions of the two eye fundus images for stereoscopic viewing are aligned for display on a monitor (see Japanese Patent No. 2844458), or photographing conditional information such as the photographed left and right eye is recorded and stored along with the photographed image (see Japanese Laid-open Patent Application No. 2002-17681).

The eye fundus is stored in a memory as an electronic image. The eye fundus image stored in the memory is enlarged or scaled down in accordance with a user-specified magnification ratio, and displayed on a monitor as a visible image, so that the eye fundus image is observed after having accordingly been scaled up or down (Japanese Laid-open Patent Application No. 1999-28189).

However, a problem arises in that the angle of view of the images captured by the fundus camera is wide (45° or 20°), thereby making the depression optic cup insufficiently visible. Images are preferably captured at an angle of view of about 10° in order to respond to such a requirement. For this reason the additional introduction of high-magnification photography lenses having an angle of view of 10° is being considered for fundus cameras. Methods for newly providing high-magnification lenses as an attachment are theoretically possible. However, problems are presented in that the cost of the apparatus increases, and photographic proficiency becomes necessary because the fixation of a patient must be skillfully directed in order for a prescribed position to be photographed. Further problems are encountered because high-magnification photography inevitably results in a large amount of light being emitted on the eye fundus during the photographic process, making the method unrealistic.

To resolve the foregoing problems, the eye fundus can be photographed using electronic imagery, the magnification ratio of the image can be increased by image processing rather than via an optical process, and so-called digital magnification may be performed, as disclosed in Japanese Laid-open Patent Application No. 1999-28189. However, in order to change the magnification after the capturing of eye fundus images of a pair consisting of a left image and a right image, a magnification-changing procedure must be performed on each image. In addition, the size of the monitor cannot be changed, leading to the problem that stereoscopic viewing cannot be performed if the center of the image to be enlarged and displayed is not set at the same location in the left and right images.

Therefore, it is an object of the invention to provide a method and apparatus for processing an eye fundus image being capable of stereoscopically observing an eye fundus with a magnification adjusted to a desired ratio with a simple configuration.

SUMMARY OF THE INVENTION

The present invention is characterized in displaying at least one of two images of a fundus of the same eye being examined that are captured and recorded with a left and right parallax; clipping from the displayed image an image in a prescribed area thereof; clipping from the other recorded image an image in an area that corresponds to the area of the clipped image; and displaying the two clipped images in a left-right alignment with a conversion to a prescribed magnification.

Furthermore, the present invention is characterized in displaying at least one of two images of a fundus of the same eye being examined that are captured and recorded with a left and right parallax; extracting from the displayed image a portion having a luminance exceeding a preset threshold value; specifying an image-clipping area on the basis of the extracted portion of the image; clipping from one of the recorded images an image in the specified image area; clipping from the other recorded image an image in an area that corresponds to the area of the clipped image; and displaying the two clipped images in a left-right alignment with a conversion to a prescribed magnification.

In the present invention, as long as a high-magnification display area is specified for one of the images to be viewed stereoscopically, clipping and high magnification conversion may be performed not only for the specified image, but also for the other image, enabling the two highly magnified images to be automatically aligned and displayed as a single image. Stereoscopic observations at high magnification can therefore readily be made of eye fundus images that are stereoscopically viewed.

Further features of the invention, its nature and various advantages will be more apparent from the accompanying drawings and following detailed description of the invention.

DESCRIPTION OF THE PREFERRED EMBODIMENTS

The present invention will now be described in detail with reference to the embodiments shown in the drawings.

Figure 1:
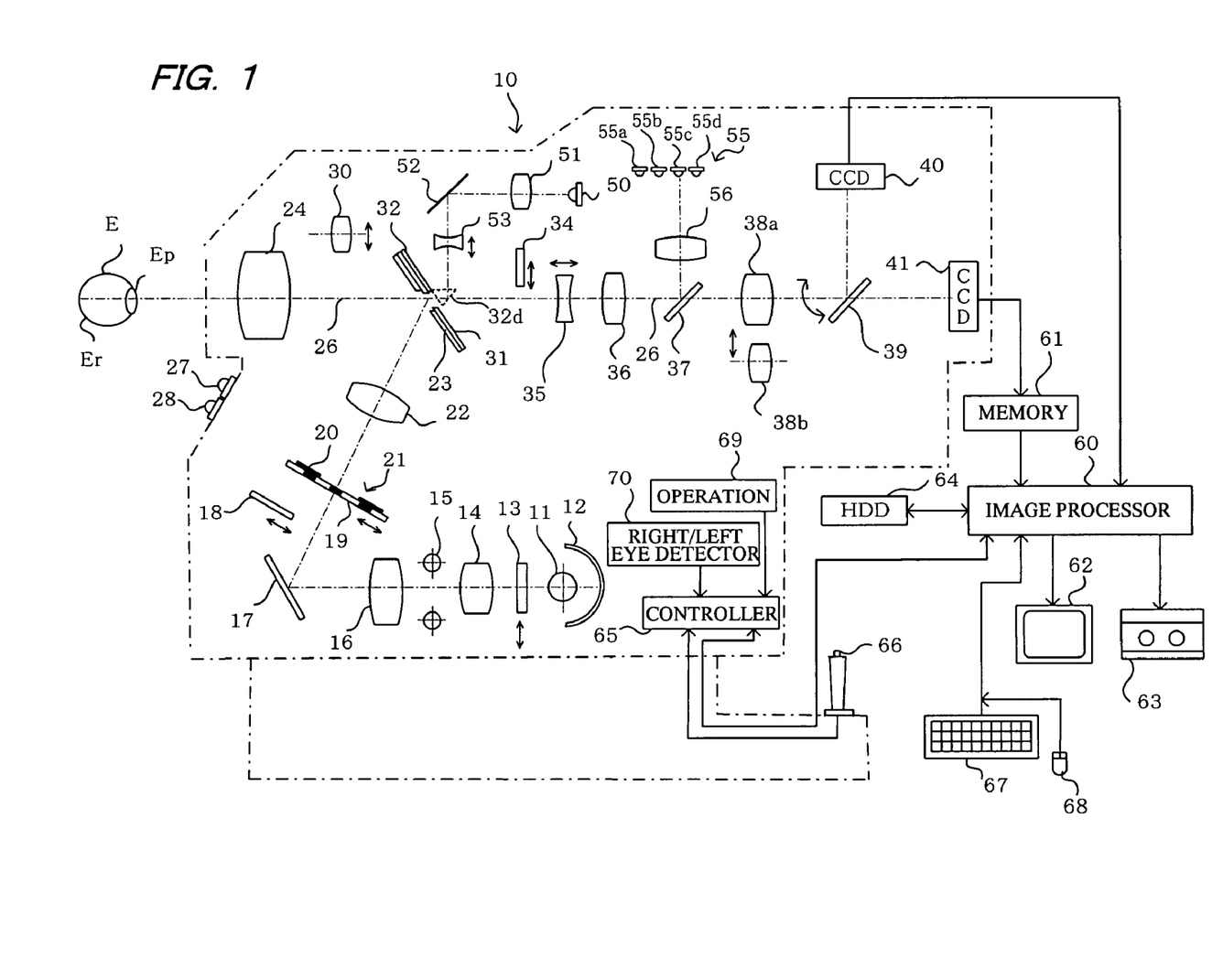
FIG. 1 is a block diagram showing an optical system of an ophthalmologic examination apparatus used in the present invention.

FIG. 1 shows a fundus camera 10 for capturing an image of a fundus of an eye being examined, recording devices (recording means) 61 and 64 for recording the captured eye fundus image, an image processor 60 for processing the captured and recorded eye fundus image, a monitor 62 for displaying the eye fundus image, a stereo monitor 63 and other components. The fundus camera 10 shown surrounded by a dashed-dotted line comprises an observation lamp 11 for emitting infrared and visible illumination light that is disposed in a center of curvature of a spherical mirror 12. Light from the observation lamp 11 and spherical mirror 12 impinges on a total reflection mirror 17 via a visible-light cutting/infrared-light transmitting filter 13 that can be inserted into and removed from the optical path, and via a condenser lens 14, a strobe light 15, and a condenser lens 16.

Illumination light reflected by the total reflection mirror 17 is transmitted through a relay lens 22 via a ring slit 21 used as an illumination stop unit that is composed of a movable illumination stop 19 and a fixed stop 20, is reflected by an apertured total reflection mirror 23, and is impinged on an anterior ocular segment (pupil) Ep of an eye being examined E via an objective lens 24. The ring slit 21 is disposed in the illumination optical system at a position substantially conjugate with the anterior ocular segment Ep (pupil) of the eye being examined, and is configured so that a variety of patterns of illumination light can be obtained in accordance with the position of the illumination stop 19.

An exciter filter 18 is inserted into or removed from the optical path of the illumination optical system during fluorescence photography.

A light source 27 composed of an infrared LED (light-emitting diode) for illuminating the anterior ocular segment Ep with infrared light is provided in order to perform alignment via the anterior ocular segment, and a light source 28 composed of an LED for illuminating the anterior ocular segment with weak white light is provided in order to capture an image of the anterior ocular segment.

Reflected light from the eye fundus Er illuminated by illumination light that has passed through the ring slit 21 is transmitted through the objective lens 24, the apertured total reflection mirror 23, a fixed stop 31, a movable stop unit 32, a focusing lens 35, an imaging lens 36, a half mirror 37, and a variable power lens 38a, and is impinged on a return mirror 39. When the return mirror 39 is positioned as shown, light reflected from the eye fundus impinges on an infrared light-sensitive CCD (image-capturing means) 40 that is in a position conjugate with the eye fundus, and the CCD 40 captures an image of the eye fundus. When the return mirror 39 is removed from the optical path, reflected light from the eye fundus impinges on a visible light-sensitive CCD (image-capturing means) 41 conjugate with the eye fundus, and an image of the eye fundus is captured by the CCD 41.

Figure 2A:
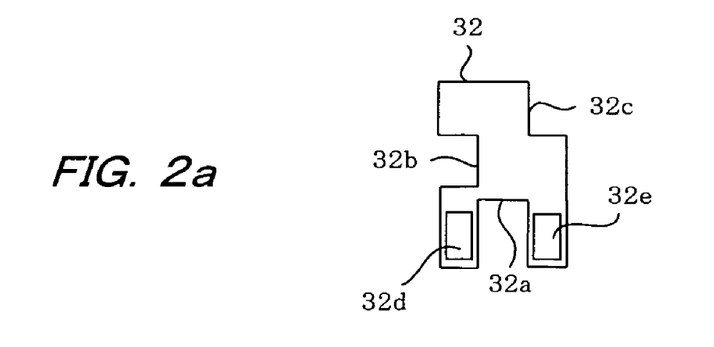
FIG. 2a is a plan view showing a configuration of a movable stop unit.
Figure 2B:
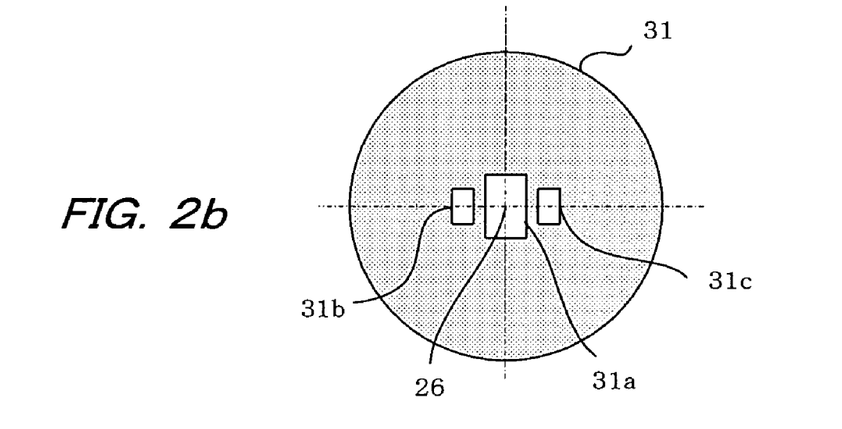
FIG. 2b is a plan view showing a configuration of a fixed stop.
Figure 2C:
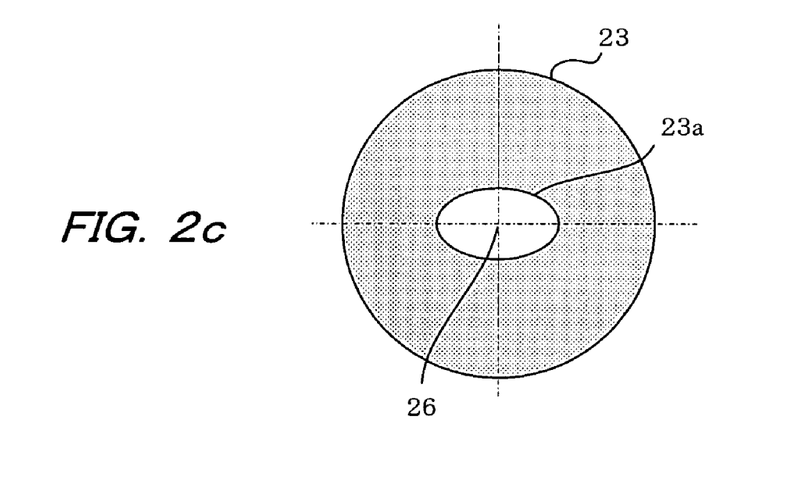
FIG. 2c is a plan view showing a configuration of an apertured total reflection mirror.

The apertured total reflection mirror 23 is a circular total reflection mirror provided with a centrally disposed horizontally elliptical aperture 23a, as shown in FIG. 2c. The fixed stop 31 is a stop provided with a centrally disposed monocular photographic stop 31a, with either side of which being provided with photographic stops (two-aperture stop) 31b and 31c for projecting a focus marker and performing stereoscopic photography, as shown in FIG. 2b. As shown in the drawings, the photographic stops 31a, 31b and 31c are formed into an oblong rectangular shape to sustain the amount of light and to minimize aberration.

The fixed stop 31 is circular in shape, has substantially the same size as the apertured total reflection mirror 23, and is affixed tightly and securely to the apertured total reflection mirror 23 while centrally aligned with the apertured total reflection mirror 23. The photographic stops 31a, 31b and 31c are provided at positions substantially conjugate with the anterior ocular segment (pupil) of the eye being examined. In this instance, the center of the photographic stop 31a is disposed in a position aligned with an optical axis 26 of the objective lens 24 (optical axis of the photographic optical system). To produce right and left images for stereoscopic viewing, the photographic optical path is laterally split at a position conjugate with the pupil, and the photographic stops 31b and 31c are respectively disposed on the left and right sides of the divided optical path. The aperture 23a of the apertured total reflection mirror 23 has a size that allows the apertures of the photographic stops 31a, 31b and 31c to be contained within the aperture 23a when the centers of the apertured total reflection mirror 23 and fixed stop 31 are in alignment.

As shown in FIG. 2a, the movable stop unit 32 has a cutaway part 32a for photographic light during monocular photography, a cutaway part 32b for the left side of the optical path during stereoscopic photography, and a cutaway part 32c for the right side optical path during stereoscopic photography. Reflection prisms 32d and 32e are provided on both sides of the cutaway part 32a to reflect a focus marker toward the eye fundus.

The movable stop unit 32 can be moved by a controller 65 in a vertical direction above the fixed stop 31 in accordance with the photography mode, as described hereafter. When the movable stop unit 32 moves to the position shown in FIG. 3a, the cutaway part 32a opens the aperture of the photographic stop 31a and selects the photographic stop 31a. When the movable stop 32 moves to the positions shown in FIGS. 3b and 3c, the cutaway parts 32b and 32c open the apertures of the photographic stops 31b and 31c, respectively, and select the photographic stop 31b or 31c. The controller 65 thus changes the photographic stop by causing the movable stop unit 32 to move in the stated order, and selects the photographic stop 31a, 31b, or 31c. For example, when a single image is captured, such as in monocular photography, the photographic stop 31a is selected; when a right-left pair of images is captured, such as in stereoscopic photography, the photographic stops 31b and 31c are selected; and in three-picture serial photography, the photographic stops 31a, 31b and 31c are selected.

Figure 3A:
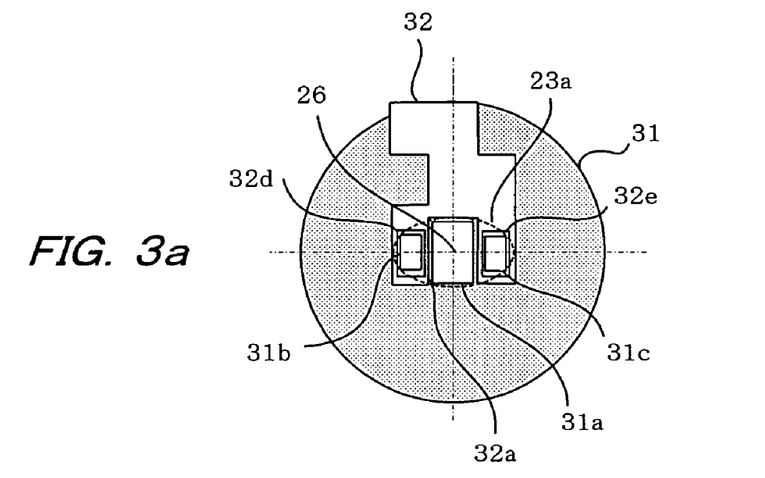
FIG. 3a through 3c are an illustrative view showing a state in which a photographic stop is selected according to the movement of the movable stop unit.
Figure 3B:
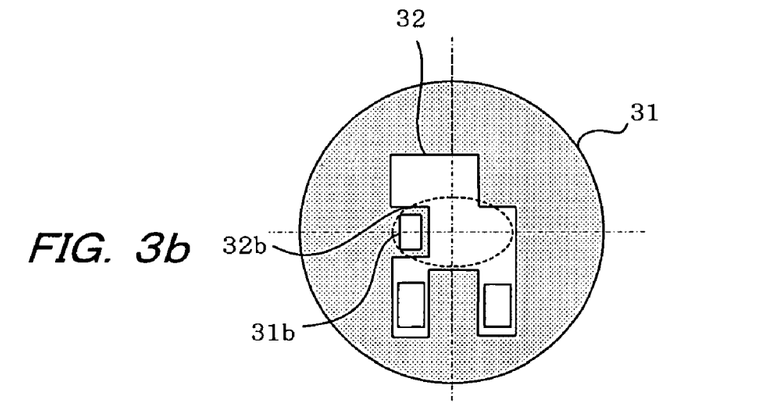
Figure 3C:
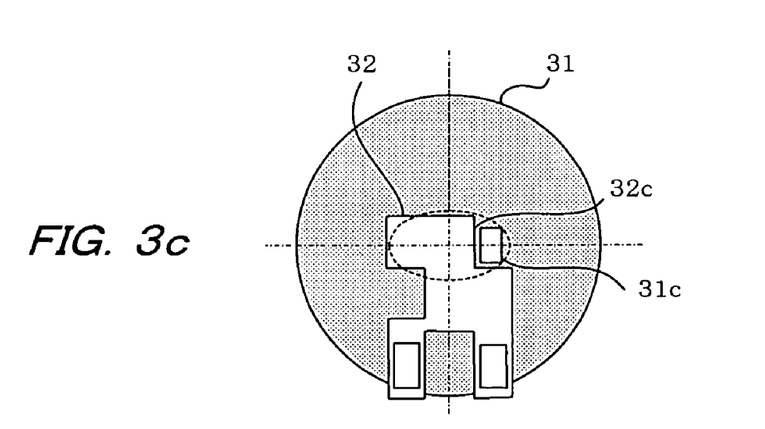

When the movable stop unit 32 is moved to the positions shown in FIGS. 3a, 3b, and 3c, the controller 65 causes the illumination stop 19 of the ring slit 21 to move in conjunction with the movable stop unit, and an illumination pattern that corresponds to the photographic mode is generated.

In FIG. 1, an anterior ocular segment lens 30 is removably disposed in the optical path between the objective lens 24 and the apertured total reflection mirror 23. When the anterior ocular segment lens 30 is inserted into the optical path, an image of the anterior ocular segment Ep illuminated by the illumination light source 27 is captured in the CCD 40 to perform alignment using the image of the anterior ocular segment Ep.

The fundus camera is further provided with a focus marker/projecting optical system in order to make it easier to bring the eye fundus into focus. In the projecting optical system, marker light from a focus-marker light source 50 composed of an infrared LED is transmitted through a lens 51, a mirror 52, and a lens 53. The optical path is then divided in two by the reflection prisms 32d and 32e secured in place to the photographic stop unit 32 to project marker light onto the eye fundus Er. The examiner can judge whether the eye fundus is in focus by determining whether there is a match between the images of the focus markers reflected by the reflection prisms 32d and 32e.

A barrier filter 34 is placed over the focus lens 35 on the side of the eye being examined during fluorescence photography.

An internal fixation lamp 55 composed of a plurality of fixation lamps 55a through 55d is provided in order to draw the fixation of the eye being examined to the fundus camera. One of the fixation lamps 55a through 55d is turned on depending on whether the photographed eye being examined is the left or right eye, and depending on the photography position of the eye fundus (e.g., near or distant from the papilla).

Light from the turned-on fixation lamp passes through a lens 56, reflected by the half mirror 37, and passes through the photographic lens 36, the focus lens 35, the photographic stop 31a (31b, 31c), the apertured mirror 23 and the objective lens 24 for projection onto the eye fundus Er. The eye being examined can therefore be kept at a predetermined position with respect to the eye fundus camera by having the patient fixate on the internal fixation lamp. In the drawings, the fixation lamps 55a through 55d are shown as being placed side-by-side on the page space. However, in actual use, the fixation lamps are placed orthogonal to the page space.

The CCD 40 captures an image of the eye fundus illuminated by infrared light that has been passed through the visible light cutting/infrared light transmitting filter 13, or an image of the anterior ocular segment illuminated by infrared light from the light source 27. The image is sent to the image processor 60, which is composed of a CPU or the like, and the resulting image is displayed as a moving image on the monitor 62. The examiner can perform alignment and adjust the focus by viewing the image displayed on the monitor 62. A stereo monitor 63 is provided as a display designed specifically for stereoscopic viewing. The examiner can view the eye fundus stereoscopically by observing the right and left images via the stereo monitor 63.

The CCD 41 captures a still image of the eye fundus illuminated by the strobe light 15 when a shutter switch 66 is operated. The eye fundus image is temporarily stored in a high-speed memory 61 and is recorded (filed) on a low-speed hard disk (HDD) 64 used as an external recording device via the image processor 60, or is displayed on the monitor 62 or stereo monitor 63.

A keyboard 67, mouse 68, or other input means is also provided. These input means can be used to input a variety of data or to specify a process for the eye fundus image stored in the memory 61, hard disk 64, or another recording device.

The controller 65, which is composed of a CPU or the like, is provided to the eye fundus camera. The controller 65 is connected to the image processor 60 for mutual signal exchange, and controls the removal of the return mirror 39 from the optical path when the shutter switch 66 is operated, further controlling the strobe light 15 so as to emit a sufficient amount of light. The controller 65 additionally controls the insertion into and removal from the optical path of the visible light cutting/infrared light transmitting filter 13, exciter filter 18, barrier filter 34, anterior ocular segment lens 30 and variable power lenses 38a, 38b, and also controls the movement of the movable stop unit 32 and the movement of the movable illumination stop 19.

An operation unit (operation panel) 69 is also provided to the eye fundus camera. The operation unit 69 has a photography mode selection switch for selecting between monocular photography, stereoscopic photography, and three-picture serial photography modes, an anterior ocular segment lens insertion/removal switch, a photography position selection switch and the like. Information related to the switches selected using the operation unit 69 is input to the controller 65.

A right/left eye detector 70 for detecting whether the photographed eye being examined is the left or right eye is further provided. The detected information concerning whether the eye is the left or right eye is input to the controller 65.

Figure 4:
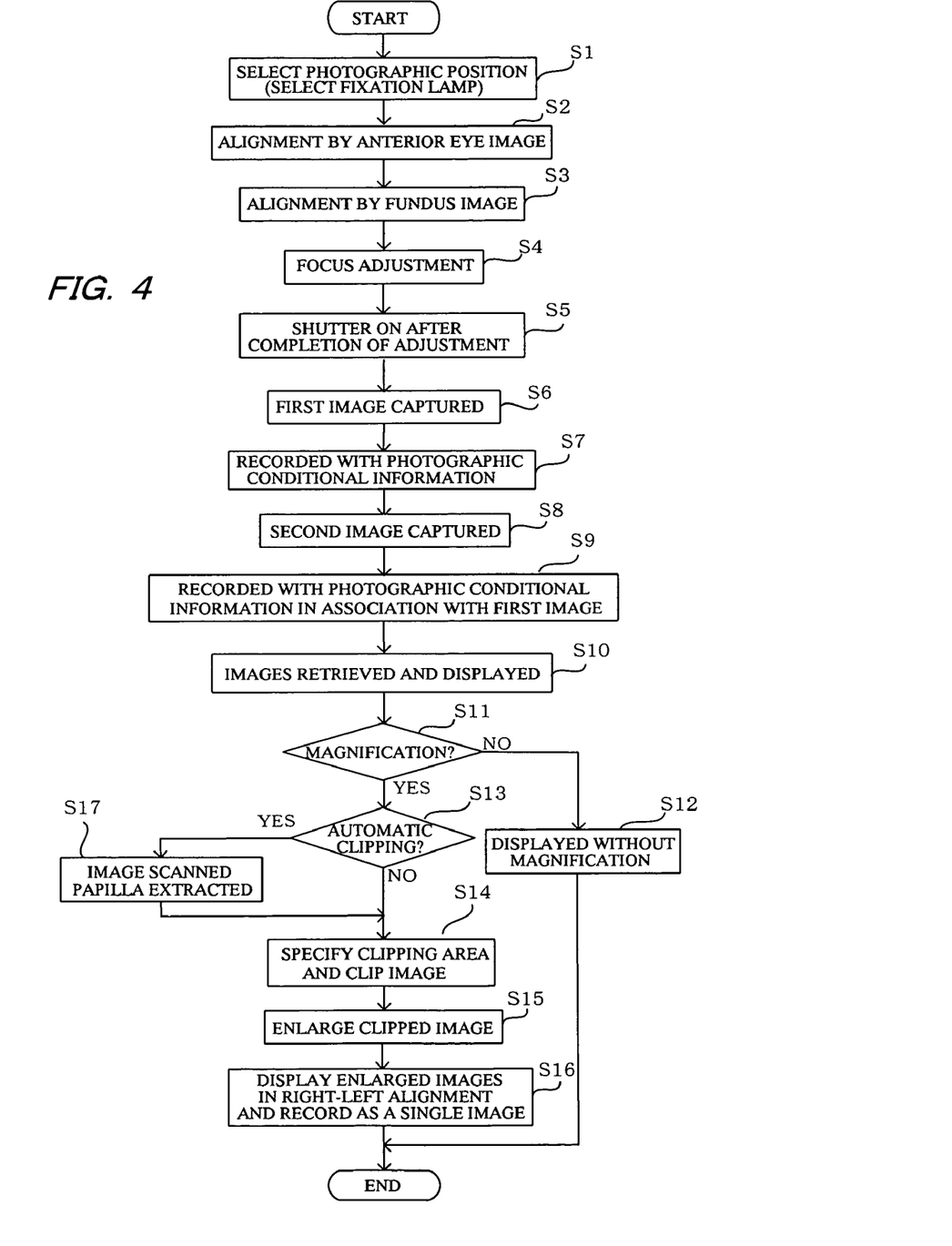
FIG. 4 is a flowchart showing the processes of photographing and displaying an eye fundus.

Processes for capturing and recording eye fundus images to be stereoscopically viewed using a fundus camera thus configured will next be described on the basis of FIG. 4, together with the displaying processes.

First, the examiner selects a position (location) of the eye fundus in the right or left eye to be photographed, and causes the person being examined to fixate by selecting and illuminating one of the fixation lamps 55a through 55d (step S1).

Next, the light source 27 is illuminated, and an image of the anterior ocular segment illuminated by the light source 27 is displayed on the monitor 62 for alignment by the anterior ocular segment (step S2). The anterior ocular segment lens 30 is then removed from the optical path, and an eye fundus image is displayed on the monitor 62, thereby enabling the examiner to perform alignment by observing the eye fundus image (step S3). The focus-marker light source 50 is then illuminated and the examiner adjusts the focus to bring the eye fundus into focus (step S4).

When the alignment by eye fundus and focus adjustment are complete, the shutter switch 66 is operated (step S5). The photographic stop 31b is then selected by moving the movable stop unit 32 to the position shown in FIG. 3b in order to obtain a left image for stereoscopic viewing. The photographic stop 31c is, however, selected when first obtaining a right image for stereoscopic viewing.

The return mirror 39 is removed from the optical path synchronically with the operation of the shutter. This causes the strobe light (flash) 15 to emit light. An image of the eye fundus illuminated by the emitted light of the strobe light 15 is transmitted through the focusing lens 35, the imaging lens 36, and the variable power lens 38a via the selected stop 31b. An eye fundus image is thus formed on the CCD 41 and captured as a first image (step S6).

The eye fundus image is then temporarily recorded in the memory 61. The image is recorded along with photographic conditions such as the ID of the eye being examined, the time and date at which the image was captured, the amount of light used in the photography (amount of light emitted by the strobe light), an indication of which eye (left or right) was photographed, the position of the photographic stop and the like (step S7).

The photographic stop 31c, which was not selected during the first image capture, is next selected, the strobe light emits light, and a right eye fundus image for stereoscopic viewing is captured as a second image (step S8). In the same manner as with the first eye fundus image, the second eye fundus image is recorded in the memory 61 in association with the first image along with the photographic conditions employed when the second image was captured (step S9).

Accordingly, only a single shutter operation is used for stereoscopic photography to switch between the photographic stops 31b and 31c (two-aperture stop) and successively create a right-left pair of eye fundus images for stereoscopic viewing. The images are then recorded along with information concerning the position of the photographic stops (e.g., right position and left position) when the images are captured.

In addition to such stereoscopic photography, the eye fundus camera of FIG. 1 also performs monocular photography and three-image photography. However, the present invention is used to obtain images that are stereoscopically viewed. Therefore, a description of these other types of photography shall be omitted. The present invention may perform fluorescence photography as well as color photography. When fluorescence photography is performed, the exciter filter 18 and barrier filter 34 are introduced into the optical path. The image recorded in the memory 61 is sent to the external recording device 64 at a predetermined timing.

When the stereoscopically captured images recorded in the memory 61 or the external recording device 64 are retrieved and displayed, the stereo monitor 63 is used to display on the left side the image with the left-position information among the left-right image pair and on the right side the image with the right-position information together with the other information concerning the photography conditions (step S10).

Figure 5:
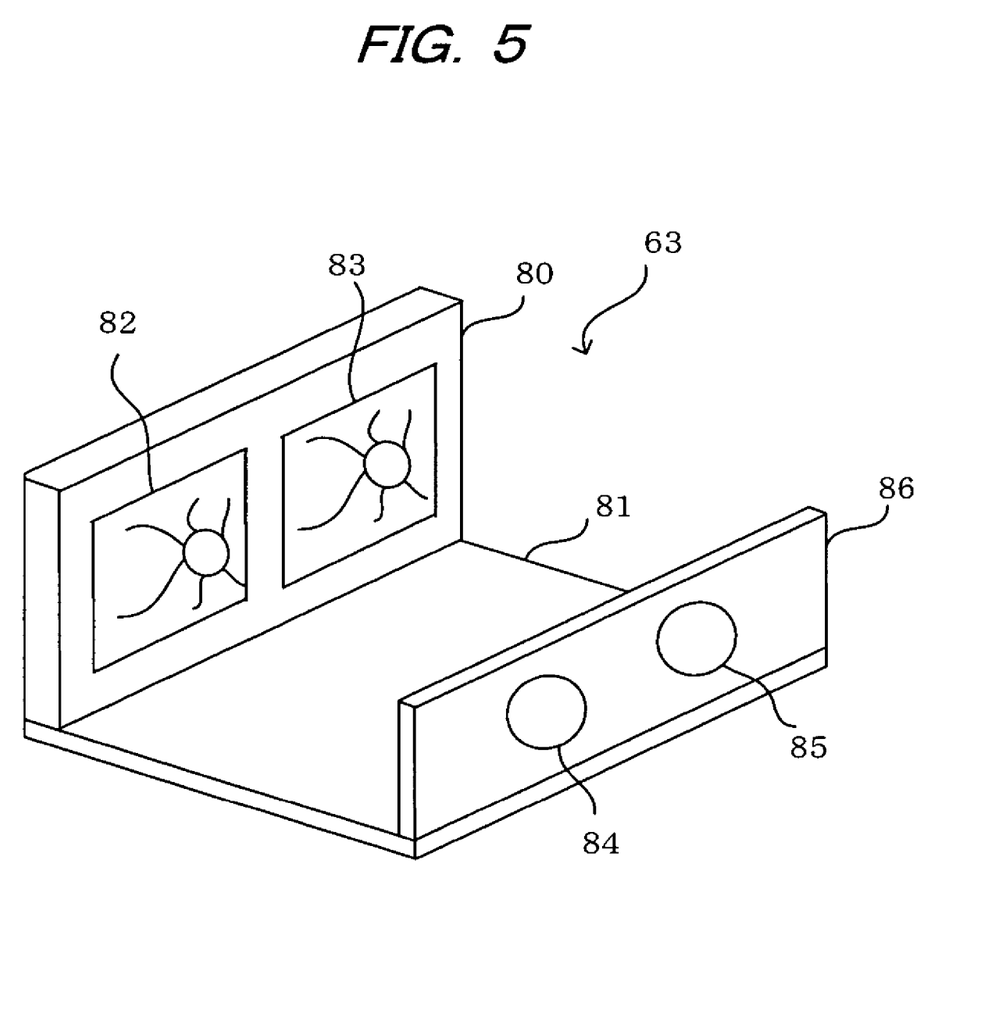
FIG. 5 is a schematic perspective view showing a configuration of a stereo monitor.

The stereo monitor 63 is shown in FIG. 5. The stereo monitor 63 includes a base plate 81 on which a display 80 is mounted to display, in a left-right alignment, the left-right pair of parallax images 82 and 83 that are captured by alternating the photographic stops. A stereoscope 86, composed of lenses or prisms 84, 85 and disposed in advance at a distance from the display 80 suitable for stereoscopic viewing, is additionally mounted on the base plate 81. During stereoscopic viewing, the examiner observes the left image 82 via the lens 84 using the left eye, and observes the right image via the lens 85 using the right eye.

If the examiner determines that no magnification is needed for stereoscopic observation ("no" in step S11), the observation will be performed without enlarging or reducing the image (step S12).

On the other hand, when stereoscopic observation is desired with a predetermined portion enlarged, either the left parallax image 82 or the right parallax image 83, or both, will be retrieved from the recording device and displayed, and the area of the image to be enlarged will be specified manually or automatically.

Figure 6:
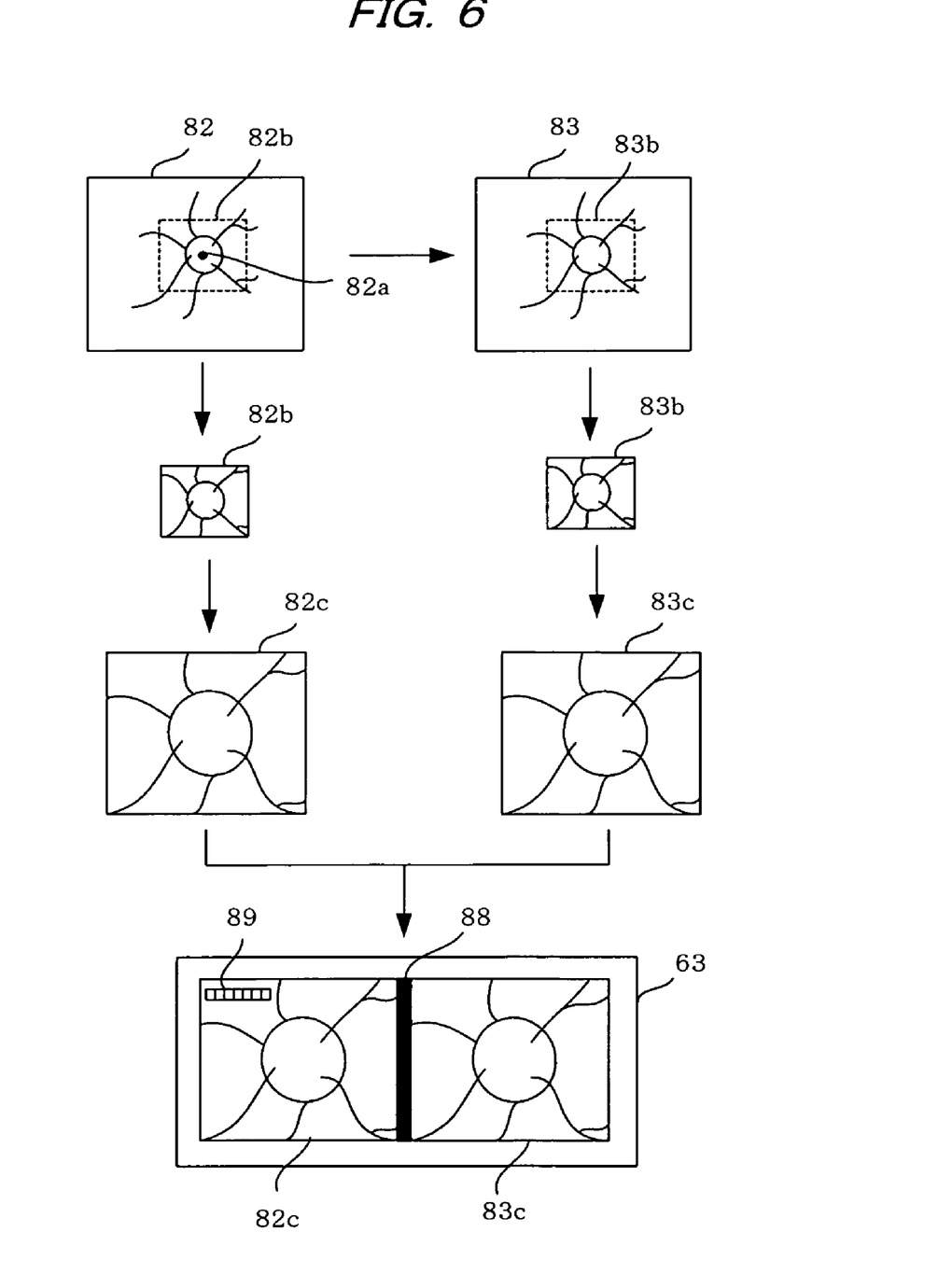
FIG. 6 is an illustrative view showing the process for manually setting a clipping area and displaying an enlarged image.

When the area to be enlarged is set manually ("no" in step S13), the mouse or the like is used to indicate a point 82a to be the center of the area of the left parallax image 82 that is to be enlarged. When the two images are displayed in an aligned fashion, the point is specified on either of the images. A predetermined clipping area (e.g., an area corresponding to an angle of view of 10°) is designated with the specified point 82a being as its center, and image data 82b within the set area is clipped (step S14).

The two images are recorded in association with one another (step S9). Therefore, if one of the images is specified, the other image can be specified based on the association. In addition, if a clipping area of one image is specified, an area of the memory region of the other image that corresponds to the memory region of this clipping area will also be determined. Therefore, image data 83b can also be clipped in the same area (the area of the same memory region) with the same number of pixels from the image i.e., the right parallax image 83 in the example of FIG. 6, that is not used (not displayed) when the central point was specified.

These clipping processes are performed by the image processor 60. The image processor 60 thus constitutes clipping means.

Both of the images 82b and 83b clipped from each of the recorded images are enlarged at the same magnification ratio to create enlarged images 82c and 83c, which are displayed on the stereo monitor 63 in a left-right alignment with a slight gap therebetween (step S16). Placing a black border 88 in the oblong portion that is the boundary between the two images 82c and 83c readily allows the images to be stereoscopically viewed. A length-determining scale 89 is placed in a corner of one of the two images through image synthesis. The resulting image for stereoscopic viewing is recorded and stored as single-image data in the recording device 64.

The clipping area may be specified by direct manipulation of the image rather than by specifying a predetermined point 82a. In addition, the image may be clipped using the normal monitor 62 rather than the stereo monitor 63.

The image was clipped manually in the above description, but the clipping area may also be determined by, for example, using a function key provided to the keyboard 67, or by displaying and operating a function button on the monitor 62 or 63.

Figure 7:
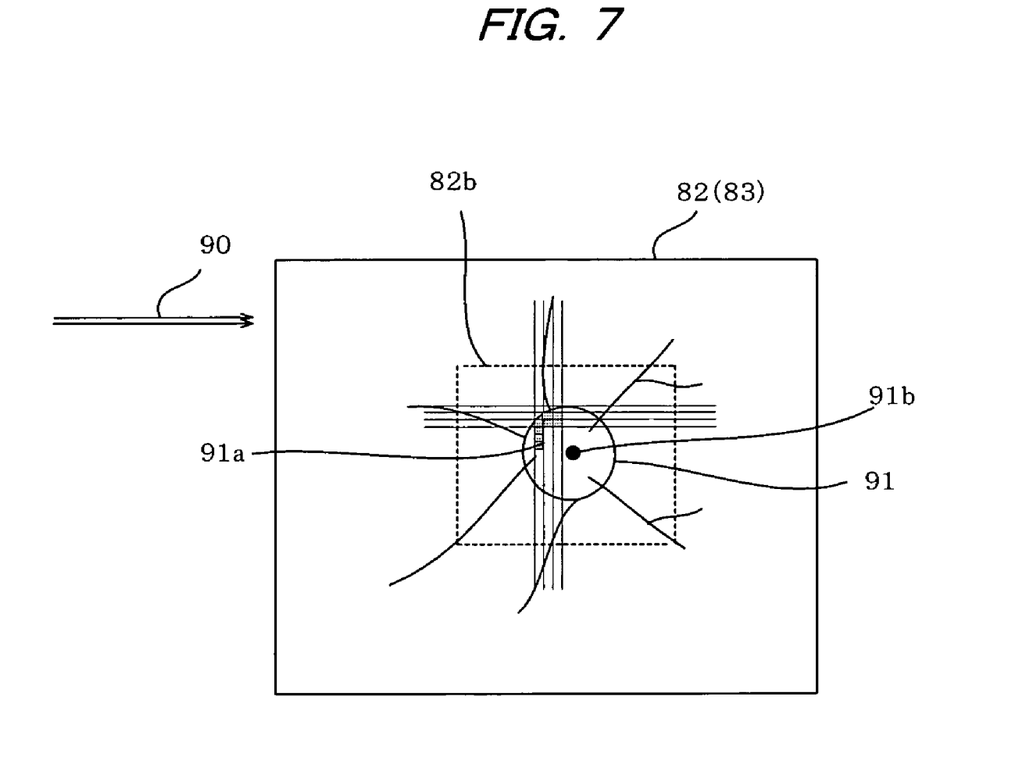
FIG. 7 is an illustrative view showing a state in which the clipping area of the image is selected by using an image scan.

An example thereof is shown in FIG. 7. First, the left parallax image 82(83) is retrieved and scanned using scanning lines 90. The image processor 60, serving as extracting means, extracts bright portions (indicated by halftone pixels 91a) having a luminance exceeding a predetermined threshold value, taking into particular account the luminance of points (pixels) in the eye fundus image (step S17). The extracted region is considered to be a papillary area 91 of the eye fundus, and a center of mass 91b of the extracted region is determined. In such circumstances, the determination need not be performed merely based on the center of mass of one image, but can be performed by applying the same process to determine the center of mass of the other image as well and derive therefrom an average value of the centers of mass.

Once the center of mass has been determined in this manner, a central position for clipping the image is selected based on the coordinates of the center of mass, and image data 82b for a predetermined area (e.g., a portion corresponding to an angle of view of 10°) is clipped from either the right parallax image or the left parallax image on the basis of the central position (step S14). Then, in the same manner as in the example shown in FIG. 6, an image in an area corresponding to the area of the clipped image is clipped from the other image. The two clipped images are then converted (enlarged) to a predetermined magnification, and displayed as a single image in a left-right alignment (steps S15, S16).

Thus, in either of the examples shown in FIG. 6 or 7, a point is specified in either of the two images to determine an image to be clipped. The image specified and the other image not specified are both processed for high magnification in the same clipped area and at the same conversion/magnification, and the images are then displayed side-by-side, and recorded and saved as a new single image.

What is claimed is:

1. A method for processing an eye fundus image, comprising the steps of:
   displaying at least one of two images of a fundus of the same eye being examined that are captured and recorded with a left and right parallax;
   extracting from the displayed image a portion having a luminance exceeding a preset threshold value;
   specifying on the basis of the extracted portion of the image an image-clipping area whose image is to be enlarged;

automatically clipping from one of the recorded images an image in the specified area;

automatically clipping from the other recorded image an image in an area that corresponds to the area of the clipped image;

processing the two clipped images for enlargement at the same magnification; and displaying the two enlarged clipped images in a left-right alignment.

2. An apparatus for processing an eye fundus image, comprising:

displaying means for displaying at least one of two images of a fundus of the same eye being examined that are captured and recorded with a left and right parallax;

extraction means for extracting from the displayed image a portion having a luminance exceeding a preset threshold value;

clipping means for automatically clipping from one of the recorded images an image to be enlarged in an area specified on the basis of the extracted image portion and automatically clipping from the other recorded image an image in an area that corresponds to the area of the clipped image; and processing means for processing the two clipped images for enlargement at the same magnification;

wherein the two enlarged clipped images are displayed in a left-right alignment.

3. An apparatus according to claim 2, wherein the clipping area is specified by deriving a center of mass of the extracted portion of the image, determining a reference position for clipping an image in accordance with coordinates of the center of mass, and setting an area having a prescribed size with its center on the reference position.

4. An apparatus according to claim 2, wherein the two clipped images are displayed with a gap of a predetermined width therebetween.

5. An apparatus according to claim 2, wherein a scale for indicating dimensions of the clipped images is displayed.

* * * * *